United States Patent [19]

Clemens

[11] Patent Number: 5,292,766
[45] Date of Patent: Mar. 8, 1994

[54] METHOD FOR IMPROVING PRIMARY MEMORY AND/OR LEARNING

[75] Inventor: James A. Clemens, Indianapolis, Ind.

[73] Assignee: Eli Lilly and Company, Indianapolis, Ind.

[21] Appl. No.: 857,521

[22] Filed: Mar. 25, 1992

[51] Int. Cl.$^5$ .................................. A61K 31/405
[52] U.S. Cl. ............................................. 514/415
[58] Field of Search ................................. 514/415

Primary Examiner—S. J. Friedman
Attorney, Agent, or Firm—Woodard, Emhardt, Naughton, Moriarty & McNett

[57] ABSTRACT

A method for improving primary memory or learning in a mammal comprising administering a 5-hydroxytryptamine receptor agonist which is selective for the 5-hydroxytryptamine-1A receptor subtype, or a pharmaceutically acceptable salt thereof.

9 Claims, No Drawings

METHOD FOR IMPROVING PRIMARY MEMORY AND/OR LEARNING

BACKGROUND OF THE INVENTION

This invention relates to a method for improving primary memory and/or learning, employing a 5-hydroxytryptamine receptor agonist which is selective for the 5-hydroxytryptamine-1-A receptor subtype.

Heretofore, various agents have been reported to improve memory. For example, these have included nicotine, caffeine, amphetamine, strychnine and picrotoxin. Additionally, fluoxetine (U.S. Pat. No. 4,647,591) and certain alpha-2I selective adrenergic receptor agonists (U.S. Pat. No. 4,847,300) have been reported as memory improving agents.

Studies have evidenced that the hippocampus plays an important role in learning and memory. Certain electrical activity exhibited by the hippocampus (electroencephalographic (EEG)), in particular the hippocampal theta rhythm (4 to 9 hertz), has been reported to be an important temporal correlate of memory storage and sensory processing. See, e.g. Landfield, P. W., J. L. McGaugh and R. J. Tusa, "Theta Rhythm: A temporal Correlate of Memory Storage Processes in the Rat", *Science* 175: 87–89, (1972); and Klemm, W. R., "Hippocampal EEG and Information Processing: A special Role for Theta Rhythm", *Prog. in Neurobiol.* 7, 197–21 (1976). Studies have also evidenced that the hippocampal theta rhythm is predictive of the rate of learning. Berry, S. D. and R. F. Thompson, "Prediction of Learning Rate from the Hippocampal ElectroencePhalogram", *Science*, 200, 1289–1300 (1978). For additional information as to the role of the hippocampus and memory, reference can be made to Paxinos, George, *The Human Nervous System*, pp. 745–746 (1990).

It is also well-known that this hippocampal theta rhythm is dependent on cholinergic activity, and treatments that inhibit cholinergic activity inhibit both the theta rhythm and short term memory. Bland, B. H., M. G. Seto, B. R. Sinclair and S. M. Fraser, "The Pharmacology of Hippocampal Theta Cells: Evidence that the Sensory Processing Correlate is Cholinergic", *Brain Research*, 229, 121–131 (1984).

Studies have also indicated that 5-hydroxytryptamine (also known as serotonin) has a role in memory and learning, and that certain serotonin reuptake inhibitors can improve memory. See, e.g., Altman, H. J. et al., "Role of serotonin in memory: Facilitation by alaproclate and zimeldine", *Psycopharm.*, 84, 496–502 (1984); and U.S. Pat. No. 4,647,591 (fluoxetine).

5-Hydroxytryptamine (hereinafter sometimes referred to as "5-HT") receptors in the central nervous system (CNS) have been the subject of substantial attention over the past decade. Multiple 5-HT receptor subtypes in the CNS have been identified. Originally, these 5-HT recognition sites were classified into two subtypes. A subset of 5-HT receptors which bound [$^3$H]-5-HT with high affinity was designated 5-HT$_1$, and a subset which bound [$^3$H]-spiperone with high affinity was designated 5-HT$_2$. See, Peroutka, S. J. and Snyder, S. H., *Mol. Pharmacol.*, 16. 687 (1979). Since then, 5-HT$_1$ receptors have been subdivided into four classes, 5-HT$_{1A}$, 5-HT$_{1B}$, 5-HT$_{1C}$, and 5-HT$_{1D}$. See, e.g., Pedigo, N. W. et al., *J. Neurochem.*, 36, 220 (1981); Hoyer, D. et al., *Eur. J. Pharmacol.*, 118, 13, 1985; Peroutka, S. J., *J. Neurochem.*, 47, 529 (1986); and Heuring, R. E. et al., *J. Neurosci.*, 7, 894 (1987). Additionally, another subtype of 5-HT receptor, the 5-HT$_3$ receptor, has been identified. Further, it has been recognized that 5-HT agonists which act at different 5-HT receptors can product opposite effects in a given system. For example, it is known that both 5-HT$_{1A}$ and 5-HT$_2$ agonists effect thermoregulation. However, 5-HT$_{1A}$ agonists produce a hypothermic response, while 5-HT$_2$ agonists produce a hyperthermic response. See, Glennon, *J. Med. Chem.*, 30, pp. 1–12 (1987). Furthermore, the differential effects of 5-HT agonists which are selective for specific subtypes is not limited to thermoregulation, but also include other physiological phenomena.

The present invention relates to the use of 5-HT receptor agonists which are selective for the 5-HT-1A subtype (i.e. selective 5-HT$_{1A}$ agonists) to improve primary memory and/or learning functions. Several such selective 5-HT$_{1A}$ agonists have been identified and reported in the literature. These selective agonists may be for instance, indoles (see. e.g. U.S. Pat. No. 4,576,959), arylpiperazines, aminotetralins, benzodioxanes, pyrimidinylpiperazines, or aryloxypropanolamines. Perhaps best known thus far is the aminotetralin, 8-hydroxy-2(di-n-propylamino)tetralin (8-OH-DPAT), which has been identified as the prototypic selective 5-HT$_{1A}$ agonist. See, e.g., Glennon, R. A., *J. Med. Chem.*, 30, 1, pp. 1–12 (1987). Several reviews on the subject exist, to which reference may be made for further information as to selective 5-HT$_{1A}$ and other 5-HT agonists. See, e.g., Robertson, D. W. et al., *Annu. Rep. Med. Chem.*, 23, pp. 49–58 (1988); Johnson, G., *Annu. Rep. Med. Chem.*, 22, 41 (1987); Fozard, J. R., *Trends Pharmacol. Sci*, 8, 501 (1987); and Green, J., *Trends Pharmacol. Sci*, 8, 90 (1987).

As to physiological effects, to date, selective 5-HT$_{1A}$ agonists have been reported to produce hyperphagia and hypothermia, to stimulate sexual behavior, to be anxiolytic, and to cause the 5-HT behavioral syndrome.

No reports have been made that selective 5-HT$_{1A}$ agonists induce hippocampal theta rhythm and thus may be used as excellently suited agents for affecting and improving primary memory and/or learning functions associated with hippocampal theta rhythm. The present invention is based on the discovery of this phenomenon.

SUMMARY OF THE INVENTION

Accordingly, one preferred embodiment of the invention relates to a method for improving primary memory or learning in a mammal, comprising administering to a mammal in need of improvement of primary memory or learning a selective 5-HT$_{1A}$ agonist, or a pharmaceutically acceptable salt thereof, at a dose which is effective to improve memory or learning.

Another preferred embodiment of the invention relates to a method for inducing hippocampal theta rhythm in a mammal, comprising administering to a mammal in need of hippocampal theta rhythm induction an effective amount of a 5-HT$_{1A}$ agonist or a pharmaceutically acceptable salt thereof.

DETAILED DESCRIPTION OF THE INVENTION

The present invention is based on the observation that administering a selective 5-HT$_{1A}$ agonist, e.g 8-OH-DPAT or (±)-4-(di-n-propyl)amino-6-methoxy-1,3,4,5-tetrahydrobenz[c,d]indole, or a pharmaceutically acceptable salt thereof, to a mammal, increases the occurrence of the hippocampal theta rhythm associated with enhanced primary memory and/or learning. In this regard, as used herein, the term "effective amount of a 5-HT$_{1A}$ agonist" means an amount of a 5-HT$_{1A}$ agonist capable of inducing hippocampal theta rhythm associated with primary memory and learning functions, or in any event an amount capable of improving primary memory and/or learning.

The active compound of the present invention, namely, a selective 5-HT$_{1A}$ agonist, is preferably administered after formulation into a pharmaceutical composition.

Pharmaceutical compositions used in the methods of this invention for administration to mammals can be prepared by known procedures using well known and readily available ingredients. The pharmaceutical compositions comprise, as an active ingredient, at least one selective 5-HT$_{1A}$ agonist, in association with a pharmaceutically acceptable carrier, diluent or excipient. In this regard, the term "pharmaceutically acceptable" means that the carrier, diluent or excipient is compatible with the other ingredients of the formulation and not deleterious to the recipient thereof.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrolidone, cellulose, water syrup, methyl cellulose, methyl-hydroxybenzoates, propylhydroxybenzoates, talc, magnesium stearate and mineral oil. The formulations may additionally include lubricating agents, wetting agents, sweetening agents, flavoring agents, coloring agents, and the like. The compositions of the invention may be formulated so as to provide quick, sustained or delayed release of the active ingredient after administration to the patient by employing procedures well known in the art, for example by including disintegrating agents, e.g. agar-agar, calcium carbonate and sodium bicarbonate, agents for retarding dissolution, e.g. paraffin, etc.

The pharmaceutical compositions can be in the form of tablets, granules, pills, dragees, powders, lozenges, sachets, cachets, elixers, suspensions, emulsions, solutions, syrups, aerosols, (as a solid or in a liquid medium), ointments, soft and hard gelatin capsules, suppositories, ampoules, sterile injectable solutions, sterile packaged powders, and the like.

The compositions are preferably formulated in a unit dosage form suitable for medical administration. The amount of active ingredient in each unit dosage will vary according to many factors, including the frequency with which the unit dosages are to be administered. In general, each unit dosage will include an amount of active ingredient that enables convenient administration of the daily dosages given below (by the administration of less than one, one, or more than one unit dosage per day). In this connection, the term "unit dosage form" refers to physically discrete units suitable as unitary dosages for human subjects and other mammals, each unit containing a predetermined quantity of active material calculated to produce the desired therapeutic effect, in association with a suitable pharmaceutical carrier and/or enclosed within an envelope. In general, the active ingredient in such pharmaceutical compositions comprises from 0.1% to 99.9% by weight of the composition.

The active compound can be administered by a variety of routes including oral, rectal, transdermal, subcutaneous, intravenous, and intramuscular, preferably oral. Preferred Pharmaceutical compositions are, therefore, those adapted for oral administration.

The specific dose of compound administered according to this invention will, of course, be determined by the particular circumstances surrounding the case, including, for example, the compound administered, the route of administration, and the condition being treated. A typical daily dose will contain from about 0.1 mg/kg to about 250 mg/kg of the active compound of this invention, more preferably from about 0.5 mg/kg to about 20 mg/kg.

As indicated, this invention is based on the observation that the administration to a mammal of a selective 5-HT$_{1A}$ agonist, e.g. 8-OH-DPAT or ($\pm$)-4-(di-n-propyl)amino-6-methoxy-1,3,4,5-tetrahydrobenz[c,d]indole, or a pharmaceutically acceptable salt thereof, induces hippocampal theta rhythm associated with primary (i.e. short-term) memory, and learning functions.

In this regard, as generally recognized, there are differing types of memory including primary memory, also known as short-term memory, and long-term memory, also known as fixed memory or permanent memory. Primary memory involves the memory of a few informational bits for a few seconds to a minute or more at a time. Information in primary memory is instantaneously available. This is contrasted to long-term memory, which involves storage in the brain of information that can be recalled at some later time such as minutes, hours, days, months or years later, and for which the mind needs to be searched for recollection. Primary memory and long-term memory have also been distinguished on a physiological basis. Mechanisms proposed for primary memory focus upon more transient conditions in the brain, while those for long-term memory focus upon actual anatomical, physical, or chemical changes in the brain. See, for example, Guyton, A. C., *Textbook of Medical Physiology*, 6th addition, pp. 690–695 (1981).

The agonist employed in the invention may be a full agonist or a partial agonist. As such, as used herein, the term "agonist" is intended to include full and partial agonists. Additionally, as used herein, the terms "selective 5-HT$_{1A}$ agonist" and "5-HT agonist which is selective for the 5-HT$_{1A}$ subtype" and the like are intended to mean that the 5-HT agonist has a greater affinity for the 5-HT$_{1A}$ subtype than for other subtypes. It is preferred that the agonist used in this invention have an affinity for the 5-HT$_{1A}$ subtype at least ten times greater than that for other subtypes, more preferably at least about 100 times greater. For example, the preferred compound 8-OH-DPAT has an affinity for the 5-HT$_{1A}$ subtype which is 1000 times greater than its affinity for other 5-HT subtypes.

It is also preferred that the agonist employed in this invention have a high affinity for the 5-HT$_{1A}$ subtype, i.e. preferred agonists bind strongly to the 5-HT$_{1A}$ subtype. More preferably the agonist employed will display a K$_i$ of about 2.0 nanomolar ("2.0 nM") or below, where K$i$ is the dissociation constant of the agonist-5-HT$_{1A}$ receptor complex. Those agonists displaying a K$_i$ of about 1.5 nM or below (e.g. 8-OH-DPAT K$_i$=1.2 nM) are most preferred. It will be understood, however, that 5-HT$_{1A}$ agonists with lower affinities than these preferred values can be employed so long as the agonists possess the ability to pass the blood-brain barrier or be administered into the brain and bind to 5-HT$_{1A}$ receptors with sufficient strength to increase the hippocampal theta rhythm.

Additional representative 5-HT$_{1A}$ agonists suitable for use in the present invention include, for example:

(±)-6-Acetyl--(di-n-propylamino)-1,3,4,5-tetrahydrobenz[cd]indole;
(±)-6-(2,2-Dimethylpropanoyl)-4-(di-n-propylamino)-1,3,4,5-tetrahydrobenz[cd]indole;
(2aS,4R)-,(2aR,4S)-6-acetyl-4-(di-n-propylamino)-1,2,2a,3,4,5-hexahydrobenz[cd]indole;
(−)-,(2aR,4R)-6-acetyl-4-(di-n-propylamino)-1,2,2a,3,4,5-hexahydrobenz[cd]indole;
(+)-(2aS,4S)-6-acetyl-4-(di-n-propylamino)-1,2,2a,3,4,5-hexahydrobenz[cd]indole;
(+)-(2aS,4R)-6-acetyl-4-(di-n-propylamino)-1,2,2a,3,4,5-hexahydrobenz[cd]indole;
(−)-(2aR,4S)-6-acetyl-4-(di-n-propylamino)-1,2,2a,3,4,5-hexahydrobenz[cd]indole;
(+)-(2aS,4R)-6-(2-methylpropanoyl)-4-(di-n-propylamino)-1,2,2a,3,4,5-hexahydrobenz[cd]indole;
(+)-(2aS,4R)-6-(benzoyl)-4-(di-n-propylamine)-1,2,2a,3,4,5-hexahydrobenz[cd]indole;
(+)-(2aS,4R)-6-(propanoyl)-4-(di-n-propylamino)-1,2,2a,3,4,5-hexahydrobenz[cd]indole;
2-Di-n-propylamino-8-(isoxazol-5-yl)-1,2,3,4-tetrahydronaphthalene;
2-Di-n-propylamino-8-isoxazol-3-yl)-1,2,3,4-tetrahydronaphthalene;
2-Di-n-propylamine-8-pentanoyl-1,2,3,4-tetrahydronaphthalene;
2-Di-n-propylamine-8-cyclohexanecarbonyl-1,2,3,4-tetrahydronaphthalene;
8-[4-[4-(2-Pyrimidinyl)-1-piperazinyl]butyl]-8-azaspiro[4.5]decane-7,9-dione (Buspirone);
4,4-Dimethyl-1-[4-[4-(2-pyrimidinyl)-1-piperazinyl]butyl]-2,6-piperidinedione (Gepirone);
2-[4-[4-(2-Pyrimidinyl)-1-piperazinyl]butyl]-1,2-benzisothiazolin-3(2H)-one 1,1-dioxide (Ipsapirone).

It will be understood that this list is by no means intended to be exhaustive and that many other suitable 5-HT$_{1A}$ agonists are known to the art and literature which are all contemplated as within the scope of the present invention.

Pharmaceutically-acceptable salts of the compounds employed in the invention include salts derived from non-toxic inorganic acids such as hydrochloric acid, nitric acid, phosphoric acid, sulfuric acid, hydrobromic acid, hydroiodic acid, phosphorous acid and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids, and the like. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propionate, oxalate, malonate, succinate, suberate, sebecate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, beta-hydroxybutyrate, glycollate, maleate, naphthalene-1-sulfonate, naphthalene-2-sulfonate, mesylate, etc.

As noted above, a number of studies have evidenced that hippocampal theta rhythm of about 4 to 9 hertz is a temporal correlate of memory storage and sensory processing, see, e.g. the above-cited works by Landfield, P. W. et al. and Klemm, W. R., and that this hippocampal theta rhythm is predictive of the rate of learning, see, e.g. the above-cited work by Berry, S. D. et al. It is also known that this hippocampal theta rhythm associated with memory storage and sensory processing can be blocked by atropine or other cholinergic antagonists. This is contrasted to another hippocampal theta rhythm, which is typically 1 to 2 Hertz higher, which can occur during locomotion (e.g. walking). This locomotion-induced theta rhythm cannot be blocked by cholinergic antagonists. As will be set forth in greater detail below, the theta rhythm induced by the method of the invention was completely blocked by pretreatment with atropine, thus further evidencing that the Present inventive method will improve memory and learning functions which are associated with the atropine-sensitive hippocampal theta rhythm.

The publications cited or otherwise referred to herein are indicative of the knowledge possessed by those ordinarily skilled in the art to which the invention pertains, and are hereby incorporated by reference in their entirety as if fully set forth.

The following Examples are given by way of illustration only and are not intended to and should not be interpreted to limit the scope of the invention in any way.

EXAMPLE 1

Methods

Male Wistar rats were implanted with depth electrodes in the CA1 area of the dorsal hippocampus and with skull screws over the frontal and parietal cortex. After recovery, the rats were adapted to the recording and injection procedures. On the day of the experiment, the EEG was recorded for a variable period of time in order to obtain samples of data from each of four behaviors: Awake and quiet, moving, non-REM sleep, and REM sleep. The EEG was recorded on a Grass polygraph and on magnetic tape. Once a suitable amount of baseline EEG was obtained, the rats were injected with 8-hydroxy-2(di-n-propylamino)tetralin (0.1, 0.3, and 1.0 mg/kg i.p.) prepared according to the procedures described in Arvidsson, L. E. et al., *J. Med Chem.*, 27, 45 (1984). The subjects' EEG's were then recorded continuously on paper and intermittently on tape for several hours, and the subjects' behaviors observed and noted.

After the experiment, the signal from the magnetic tape was fed into a Hewlett-Packard Dynamic Signal Analyzer. The continuous record was broken into discrete eight-second epochs. For each epoch, a Fast Fourier Transform was performed and a power spectrum (uV$_2$ vs. frequency) was constructed. The power spectra for several minutes of data were then averaged together.

For the baseline data, a length of the record of several minutes duration that consisted of only one type of behavior was fed into the signal analyzer and a map of the eight-second power spectra was constructed (time on the z-axis) and averaged to get a single power spectrum corresponding to that behavior.

After drug injection, the EEG was recorded continuously on paper and on tape for the first thirty minutes and then for ten minutes every hour on the hour for several hours. Lengths of record corresponding to a single behavior were again isolated and analyzed.

Results

The predominant effect of the administration of 8-OH-DPAT on the hippocampal EEG was the induction of a persistent, low-frequency theta rhythm that accompanied a behavioral state of waking immobility. Normally, this theta rhythm is present only infrequently during this type of behavior. The theta rhythm observed was lower in frequency by 1 to 2 Hertz than the atropine-resistant theta rhythm seen during walking.

EXAMPLE 2

In addition to the 8-OH-DPAT experiment reported in Example 1, another analogous experiment was conducted, this time using another 5-HT agonist known to be selective for the 5-HT$_{1A}$ subtype, ($\pm$)-4-(di-n-propyl)amino-6-methoxy-1,3,4,5-tetrahydrobenz[c,d]indole, prepared according to the procedures described in European Patent Application 153083 (published 1985). Again, the predominant effect on the hippocampal EEG was the induction of a persistent low-frequency theta rhythm that accompanied a behavioral state of waking immobility. Further, the theta rhythm observed was again lower in frequency by 1 to 2 Hertz than the atropine-resistant theta rhythm.

EXAMPLE 3

The 1.0 mg/kg procedure of Example 1 was repeated two times, except each time the subjects were pretreated with 50 mg/kg i.p atropine, sulfate salt. A review of the resulting EEG's revealed that the ability of the 8-OH-DPAT to induce the hippocampal theta rhythm was completely blocked.

Additional Exemplary 5-HT$_{1A}$ Agonists

The following Examples provide illustrative preparations of additional representative 5-HT$_{1A}$ agonists which, when administered as in Examples 1 and 2 above, induce a persistent, low frequency theta rhythm that accompanies waking immobility. These agonists are also suitable for use in the methods of the invention.

EXAMPLE 4

Preparation of
($\pm$)-6-Acetyl-
-(di-n-propylamino)-1,3,4,5-tetrahydrobenz[cd]indole.

A. Preparation of
($\pm$)-6-Cyano-1-triisopropyl-silyl-4-(di-n-propylamino)-1,3,4,5-tetrahydrobenz[cd]indole To a suspension of 1.00 g (6.0 mmol) of potassium hyride (24% dispersion in mineral oil) in 25 mL of THF at 0° C. were added 0.90 g (3.20 mmol) of 6-cyano-4-(di-n-Propylamino)-1,3,4,5-tetrahydrobenz[cd]indole. After stirring for 30 min, an addition of 1.00 mL (3.72 mmol) of triisopropylsilyl triflate was made. The mixture was then stirred at room temp. for 15 hours. It was then poured into cold water, and the product was extracted into CH$_2$Cl$_2$. This extract was washed with NaCl solution and dried over Na$_2$SO$_4$. Evaporation of the CH$_2$Cl$_2$ left a brown oil which was chromatographed over 15 g of silica gel using successively 1:1 hexane/toluene, toluene, and then 1:19 EtOAc/toluene. The silylated product from the column was a light brown oil weighing 0.85 g (61% yield). The product slowly crystallized upon standing.

B. Preparation of
($\pm$)-6-Acetyl-
-triisopropylsilyl-4-(di-n-propylamino)-1,3,4,5-tetrahydrobenz[cd]indole A solution of 0.30 g (0.69 mmol) of the above nitrile in 10 mL of benzene was treated with 2.0 mL of 1.0 M methylmagnesium bromide in diethyl ether. This mixture was heated at 65° C. for 15 hours. After cooling, the excess Grignard reagent was decomposed with ice chips. The mixture was then stirred for an hour with 10 mL of saturated NH$_4$Cl solution. The benzene layer was separated, and the aqueous layer was extracted with fresh benzene. The combined organic solutions were dried over Na$_2$SO$_4$ then evaporated to a viscous oil. Chromatography of this oil over 5.0 g of silica gel using 1:9 EtOAc/toluene followed by 1:1 EtOAc/toluene afforded 0.29 g (93% yield) of 6-acetyl compound as a pale yellow oil which slowly crystallized upon standing.

C. A solution of 0.10 g (0.22 mmol) of the above ketone in 2.5 mL of THF at 0° C. was treated with 0.5 mL of 1 M tetrabutylammonium fluoride in THF. After stirring for 30 minutes, the solution was poured into 10 mL of water containing 0.2 g of tartaric acid. This solution was washed with CH$_2$Cl$_2$, and these washings were extracted with fresh dil. tartaric acid solution. The combined aqueous solutions were basified with 1 N NaOH solution, and the product was extracted with CH$_2$Cl$_2$. After drying the extract over Na$_2$SO$_4$, the solvent was evaporated leaving a crystalline residue. Recrystallization from toluene/hexane afforded 0.045 g (68% yield) of ($\pm$)-6-acetyl-4-(di-n-propylamino)-1,3,4,5-tetrahydrobenz[cd]indole, mp 148.5°–150° C.

Analysis for (C$_{19}$H$_{26}$N$_2$O):
Theory: C, 76.47; H, 8.78; N, 9.39.
Found: C, 76.24; H, 8.85; N, 9.58.
NMR: (300 MHz, CDCl$_3$) δ9.90 (t, 6H, CCH$_3$ of NPr), 1.48 (sextet, 4H, CH$_2$Me), 1.57 (s, 3H, COCH$_3$), 2.58 (sextet, 4H, CH$_2$Et), 2.78 (dd, 1H, 3α-H), 2.97 (dd, 1H, 3 -H), 3.07 (dd, 1H, 5α-H), 3.20 (mult, 1H, 4 -H), 3.71 (dd, 1H, 5 -H), 6.89 (s, 1H, 2-H), 7.15 (d, 1H, 8-H), 7.66 (d, 1H, 7-H), 8.00 (s, 1H, 1-H).

EXAMPLE 5

Preparation of($\pm$)-6-(2,2-Dimethylpropanoyl)-4-(di-n-propylamino)-1,3,4,5-tetrahydrobenz[cd]indole A. Preparation of
($\pm$)-6-Bromo-1-triisopropylsilyl-4-(di-n-propylamino)-1,3,4,5-tetrahydrobenz[cd]indole To a suspension of 1.25 g (7.50 mmol) of potassium hydride (24% dispersion in mineral oil) in 50 mL of THF at 0° C. was added a solution of 2.00 g (5.97 mmol) of 6-bromo-4-(di-n-propylamino)-1,3,4,5-tetrahydrobenz[cd]indole in 2 mL of THF. After stirring for 40 min, an addition of 1.90 mL (7.18 mmol) of triisopropylsilyl triflate was made. Stirring was continued for another hour. The mixture was then poured into cold NaHCO$_3$ solution, and the product was extracted into CH$_2$Cl$_2$. This extract was washed with NaCl solution and dried over Na$_2$SO$_4$. Evaporation of the CH$_2$Cl$_2$ left a brown oil which was chromatographed over 50 g of silica gel using toluene followed by 1:3 EtOAc/toluene. The silylated product from the column was isolated as a light brown oil in quantitative yield. The product slowly crystallized upon standing.

B. Preparation of (±)-6-(2,2-Dimethyl-propanoyl)-1-triisopropylsilyl-4-(di-n-propylamino)-1,3,4,5-tetrahydrobenz[cd]indole A solution of 0.50 g (1.02 mmol) of the above 1-silylated compound in 20 mL of diethyl ether was stirred at −65° C. as 1.50 mL (2.31 mmol) of 1.54 M t-butyllithium (in pentane) was added. After stirring at −70° C. for another 30 minutes, a rapid addition of 0.50 mL (4.00 mmol) of 2,2-dimethylpropaonyl chloride was made. The mixture was allowed to warm to −10° C. It was then shaken with 50 mL of cold $NaHCO_3$ solution for several minutes, and the product was extracted into diethyl ether. This extract was washed with NaCl solution and dried over $Na_2SO_4$. Evaporation of the ether left an oil which was chromatographed over 7 g of silica gel using 1:19 EtOAc/Toluene and then 1:9 EtOAc/toluene. The product from the column was a viscous oil weighing 0.357 g (74% yield).

C. A solution of 0.345 g (0.70 mmol) of the above ketone in 7.0 mL of THF at 0° C. was treated with 1.5 mL of 1 M tetrabutylammonium fluoride in THF. After stirring for 30 minutes, the solution was poured into 25 mL of water containing 0.5 g of tartaric acid. This solution was washed with $CH_2Cl_2$, and these washings were extracted with fresh dil. tartaric acid solution. The combined aqueous solutions were basified with 5 N NaOH solution, and the product was extracted with $CH_2Cl_2$. After drying the extracted over $Na_2SO_4$, the solvent was evaporated and the residual oil was chromatographed over 7 g of silica gel using 1:9 EtOAc/toluene. The product from the column crystallized when triturated with hexane. Recrystallization from hexane afforded 0.175 g (88% yield) of (±)-6-(2,2-dimethyl-propanoyl)-4-(di-n-propylamino)-1,3,4,5-tetrahydrobenz[cd]indole, mp 92° C.

Analysis for ($C_{22}H_{32}N_2O$): Theory: C, 77.60; H, 9.47; N, 8.23. Found: C, 77.69; H, 9.37; N, 8.17.

NMR: (300 MHz, $CDCl_3$) δ0.89 (t, 6H, $CCH_3$ of NPr), 1.31 (s, 9H, $CCH_3$ of $Bu_t$)m 1.45 (sextet, 4H, $CH_2Me$), 2.53 (t, 4H, $CH_2Et$), 2.79 (dd, 1H, 3α-H), 2.94 (mult, 2H, 5-$CH_2$), 2.95(dd, 1H, 3β-H), 3.21 (mult, 1H, 4β-H), 6.87 (s, 1H, 2-H), 7.09 (d, 1H, 8-H), 7.19 (d, 1H, 7-H), 7.91 (s, 1H, 1-H).

EXAMPLE 6

Preparation of mixture of (2aS,4R)-,(2aR,4S)-6-acetyl-4-(di-n-propylamino)-1,2,2a,3,4,5-hexahydrobenz[cd]indole A. Preparation of mixture of (2aS,4R)-,(2aR,4S)-1-Benzoyl-6-cyano-4-(di-n-propylamino)-1,2,2a,3,4,5-hexahydrobenz[cd]indole To a solution of dimethyl formamide (100 mL) containing a mixture of (2aS,4R)- and (2aR,4S)-1-benzoyl-6-bromo-4-(di-n-propylamino)-1,2,2a,3,4,5-hexahydrobenz[cd]indole under a $N_2$ atmosphere were added 3.4 g (37.5 mmol) of CuCN and 7.1 g (37.5 mmol) of CuI. The reaction mixture was then stirred at 140° C. for 6 hours. The reaction mixture was poured onto ice, diluted with water, $CH_2Cl_2$ was added and the mixture stirred for 30 minutes. The mixture was filtered through a diatomaceous earth (tradename "Celite") pad and the filtrate was extracted twice with $CH_2Cl_2$. The organic solution was dried over $MgSO_4$ and then evaporated to provide 4 g of solid. Chromatography of this crude product over silica gel with 1:19 $MeOH/CH_2Cl_2$ as eluent gave 3 g (62%) of product.

B. Preparation of mixture of (2aS,4R)-,(2aR,4S)-6-cyano-4-(di-n-propylamino)-1,2,2a,3,4,5-hexahydrobenz[cd]indole To a stirred solution of 4.8 g (0.0124 mol) of 1-benzoyl-6-cyano-4-(di-n-propylamino)-1,2,2a,3,4,5-hexahydrobenz[cd]indole prepared as in Part A hereof in 200 mL of THF cooled to −78° C. under $N_2$ atmosphere, were added 16 mL (0.025 mol) of 1.6 M solution of n-butyl-lithium in hexane. The reaction mixture was stirred at −78° C. for 30 minutes and then allowed to warm to −20° C. To the reaction mixture was added 100 mL of 1 N HCl. The mixture was extracted once with ethyl ether. The acidic solution was made alkaline with the addition of cold 5 N NaOH. The basic mixture was extracted twice with $CH_2Cl_2$. The combined organic solution was washed with saturated aqueous NaCl solution. The $CH_2Cl_2$ solution was dried over $MgSO_4$ and evaporated to give 4 g of an oil. Chromatography of this oil over silica gel with ethyl acetate as eluent gave 3 g (85%) of product as an oil, which upon standing solidified.

C. Preparation of mixture of (2aS,4R)-,(2aR,4S)-6-acetyl-4-(di-n-propylamino)-1,2,2a,3,4,5-hexahydrobenz[cd]indole A solution of 0.5 g (1.8 mmol) of 6-cyano-4-(di-n-propylamino-1,2,2a,3,4,5-hexahydrobenz[cd]indole prepared as in Part B hereof in 75 mL of benzene was treated with 5 mL of 2.0 M methylmagnesium bromide in diethyl ether. The reaction mixture was refluxed for 2 days. The reaction mixture was cooled and excess Grignard reagent was decomposed with addition of saturated aqueous $NH_4Cl$ solution. The benzene layer was separated as washed once with saturated aqueous NaCl solution. The organic solution was evaporated to an oil. The oil was dissolved in 25 mL of 5 N HCl and the solution was stirred at room temperature for 30 minutes. The acidic solution was made alkaline with the addition of excess concentrated aqueous $NH_4OH$ solution. The basic mixture was extracted twice with $CH_2Cl_2$. The combined organic solution was washed once with saturated aqueous NaCl solution and dried over $MgSO_4$. The $CH_2Cl_2$ solution was evaporated to yield 0.5 g of an oil. Chromatography of this oil over silica gel with ethyl acetate as eluent gave 0.4 g (75%) of product as an oil, which upon standing solidified, m.p. 76°-77° C.

Analysis for ($C_{19}H_{28}N_2O$):
Theory: C, 75.96; H, 9.39; N, 9.32.
Found: C, 75.66; H, 9.33; N. 9.38.
NMR: (300 MHz, $CDCl_3$) d 0.89 (t, 6H, $CCH_3$), 1.46 (mult, 5H, 3α-H and $CH_2Me$), 2.16 (br d, 1H, 3β-H), 2.49 (mult, 4H, $CH_2Et$), 2.50 (s, 3H, $COCH_3$), 2.87 (dd, 1H, 5α-H), 3.15 (mult, 1H, 2α-h), 3.19 (mult, 2H, 2α-H and 2β-H), 3.42 (dd, 1H, 5β-H), 3.73 (mult, 1H, 4-H), 4.04 (br s, 1H, 1-H), 6.43 (d, 1H, 8-H), 7.63 (d, 1H, 7-H). M.S.: m/e=300 (fd).

EXAMPLE 7

Preparation of (2aR,4R)-6-acetyl-4-(di-n-propylamino)-1,2,2a,3,4,5-hexahydrobenz[cd]indole A. A mixture of 1-benzoyl-4,5-(endo)epoxy-1,2,2a,3,4,5-hexahydrobenz[cd]indole (21 g, 0.076 mol)

and (+)-R-1-phenethylamine (18 g, 0.15 mol) in 400 ml of n-butanol was refluxed under N₂ for 16 h. The reaction was concentrated in vacuo to provide 30 g of an oil as an equal. mixture of two diastereomeric amino alcohols The mixture of amino alcohols was dissolved in 300 ml of CH₂Cl₂ and Et₃N (30 g, 0.225 mol) was added at once under N₂. The reaction mixture was cooled to −10° C. then MsCl (12.9 g, 0.011) was slowly added dropwise. The rate of addition was such as to maintain a reaction temperature between −10° C. and 5° C. Upon complete addition of MsCl, the reaction mixture was stirred for an additional 30 min at −5° and then 30 min at ambient temperature. To the reaction mixture were added 200 ml of water and the mixture was stirred. The CH₂Cl₂ solution was separated and washed successively with sat'd NaHCO₃ sol and brine sol. The organic sol was dried (MgSO₄) and concentrated to dryness to provide a mixture of two diastereomeric aziridines. The mixture was separated by preparative HPLC (silica gel; hexanes/ EtOAc gradient). The first diastereomer of the aziridines to be eluted was designated isomer 1; 6.6 g, mp 162°–163° C. from i-PrOH. The second diastereomer to be eluted was designated as isomer 2; 7.4 g, mp 144°–145° C. from isopropyl alcohol.

B.
(2aR,4R)-4-amino-1-benzoyl-1,2,2a,3,4,5-hexahydrobenz[cd]indole

A solution of aziridine isomer 1 (9.4 g, 0.025 mol) in 90 ml of glacial acetic acid was hydrogenated at 60 psi and at 60° C. over 5% Pd/C for 16 h. The reaction mixture was filter and the filtrate was evaporated to a residual oil. The residue was dissolved in 1 N HCl and the acidic mixture was extracted once with EtOAc. The acidic solution was made alkaline with addition of concentrated NH₄OH. The basic mixture was extracted with CH₂Cl₂. The CH₂Cl₂ solution was washed with brine solution ad dried (MgSO₄). The organic solution was evaporated to dryness to provide 2aR,4R-4-amino-1-benzoyl-1,2,2a,3,4,5-hexahydrobenz[cd]indole; 5.2 g as an oil.

C.
(2aR,4R)-4-amino-1-benzoyl-6-bromo-1,2,2a,3,4,5-hexahydrobenz[cd]indole

A solution of (2aR,4R)-4-amino-1-benzoyl-1,2,2a,3,4,5-hexahydrobenz[cd]indole (5.2 g, 0.019 mol) and sodium acetate (6.2 g, 0.076) in 40 mL glacial acetic acid (HOAc) and 10 mL of MeOH was cooled to 10° C. To the reaction mixture was added dropwise a solution of bromine (3 g, 0.019 mol) in 10 mL of glacial HOAc. The reaction temperature was maintained at 10° C. during addition of the bromine. The reaction was then stirred at ambient temperature for 1 h. The solvents were evaporated and the residue was dissolved in water. The acidic solution was made alkaline with cold 50% aqueous NaOH. The basic mixture was extracted twice with CH₂Cl₂. The organic solution was washed with brine solution, dried (MgSO₄) and concentrated in vacuo to provide 6.8 g (2aR, 4R)-6-bromo compound as an oil.

D.
(2aR,4R)-1-benzoyl-6-bromo-4(di-*n*-propylamino)-1,2,2a,3,4,5-hexahydrobenz[cd]indole A reaction mixture of (2aR,4R)-4-amino-1-benzoyl-6-bromo-1,2,2a,3,4,5-hexahydrobenz[cd]indole (6.8 g, 0.019 mol), K₂CO₃ (8.28 g, 0.06 mol) and n-propyliodide (10.2 g, 0.06 mol) in 200 mL of CH₃CN was stirred at reflux temperature for 16 h. The reaction mixture was filtered and solvent was evaporated. The residue was dissolved in EtOAc and the solution was extracted with dilute HCl. The acidic solution was made alkaline with concentrated NH₄OH. The basic mixture was extracted with EtOAc. The organic solution was washed with brine solution and dried (MgSO₄). The EtOAc was evaporated to provide a residual oil. Chromatography (silica gel-EtOAc) gave product, 2.4 g.

E.
(2aR,4R)-1-Benzoyl-6-cyano-4-(di-*n*-propylamino)-1,2,2a,3,4,5-hexahydrobenz[cd]indole To a solution of (2aR,4R)-1-Benzoyl-6-bromo-4-(di-*n*-propylamino)-1,2,2a,3,4,5-hexahydrobenz[cd]indole (2.4 g; 5 mmol) in 100 mL of dimethyl formamide (DMF) was added CuCN (1.34 g, 15 mmol) and CuI (2.85 g, 15 mmol). The reaction mixture was stirred at reflux under a N₂ atmosphere for 16 hr. The reaction mixture was poured into 500 mL of water. The ppt was collected and washed several times with water. The ppt was suspended in dil NH₄OH and slurried with EtOAc. The whole mixture was filtered thru a celite pad. The EtOAc sol was separated and washed with brine sol. The EtOAc sol was dried (MgSO₄) and conc to dryness to provide 1.7 g of nitrile as an oil.

F.
(2aR,4R)-6-Cyano-4-(di-*n*-propylamino)-1,2,2a,3,4,5-hexahydrobenz[cd]indole To a stirred solution of 1.7 g (4.4 mmol) of (2aR,4R)-6-cyano-4-(di-*n*-propylamino)-1,2,2a,3,4,5-hexahydrobenz[cd]indole in 25 mL of THF cooled to −78° C. under a N₂ atmosphere were added 5.5 mL (8.8 mmol) of 1.6 M solution of n-BuLi in hexane. The reaction mixture was stirred at −78° C. for 30 min and then allowed to warm to −20° C. To the reaction mixture were added 20 mL of 1 N HCl. The mixture was extracted once with Et₂O. The acidic solution was made alkaline with the addition of cold 5 N NaOH. The basic mixture was extracted twice with CH₂Cl₂. The combined organic solution was washed with sat'd NaCl solution. The CH₂Cl₂ solution was dried over MgSO₄ and evaporated to give 1.3 g of an oil. Chromatography of this oil over silica gel with EtOAc as eluent gave 1 g (80%) of product as an oil.

G.
(2aR,4R)-6-Trityl-6-cyano-4-(di-*n*-propylamino)-1,2,2a,3,4,5-hexahydrobenz[cd]indole To a sol of (2aR,4R)-6-cyano-4-(di-*n*-propylamino)-1,2,2a,3,4,5-hexahydrobenz[cd]indole (1 g, 3.5 mmol) and Et₃N (354 mg, 3.5 mmol) in 50 mL of methylene chloride was added a sol of triphenylmethyl chloride (trityl chloride) (0.98 g, 3.5 mmol) in 10 mL of methylene chloride dropwise at RT. The reaction mixture was stirred for 16 hr at RT. The reaction mixture was extracted with water and cold 1 N HCl. The organic sol was washed with sat'd NaHCO₃ sol and with sat'd brine sol. The organic sol was dried (MgSO₄) and conc to dryness in vacuo to give a residue. The residue was slurried with warm hexanes, cooled and filtered to remove insolubles. The filtrate was conc to an oil. The oil was chromatographed (silica gel, 20% EtOAc in hexanes) to provide 1.5 g of (2aR,4R)-1-trityl-6-cyano-4-

(di-n-propylamino)-1,2,2a,3,4,5-hexahydrobenz[cd]indole.

H.
(2aR,4R)-6-acetyl-4-(di-n-propylamino)-1,2,2a,3,4,5-hexahydrobenz[cd]indole A solution of 1.6 g (3 mmol) (2aR,4R)-6-trityl-6-cyano-4-(di-n-propylamino)-1,2,2a,3,4,5-hexahydrobenz[cd]indole in 100 ml of THF was treated with 20 mL of 2.0 M methylmagnesium bromide in diethyl ether. The reaction mixture was refluxed for 16 hr. The reaction mixture was cooled and excess Grignard reagent was decomposed with addition of sat'd $NH_4Cl$ solution. The reaction mixture was extracted with EtOAc. The organic solution was evaporated to an oil. The oil was dissolved in 25 mL of 5 N HCl and the solution was stirred at room temperature for 30 min. The acidic solution was made alkaline with the addition of excess conc $NH_4OH$ solution. The basic mixture was extracted twice with EtOAc. The combined organic solution was washed once with sat'd NaCl solution and dried over $MgSO_4$. EtOAc solution was evaporated to yield 0.9 g of an oil. Chromatography of this oil over silica gel with EtOAc as eluent gave 600 mg of product. Recryst from hexanes to yield 2289 mg (−) ketone. mp 85°–86°; $[\alpha]_D = -4.94°$ ($CH_3OH$).

EXAMPLE 8
Preparation of (2aS,4S)-6-acetyl-4-(di-n-propylamino)-1,2,2a,3,4,5-hexahydrobenz[cd]indole A. Aziridine isomer 2 from Example 7A (8.5 g, 0.022 mol) was hydrogenated to provide (2aS,4S)-4-amino-1-benzoyl-1,2,2a,3,4,5-hexahydrobenz[cd]indole (4.5 g) as an oil

B.
(2aS,4S)-4-amino-1-benzoyl-6-bromo-1,2,2a,3,4,5-hexahydrobenz[cd]indole Using the procedure of Example 7C, (2aS,4S)-4-amino-1-benzoyl-1,2,2a,3,4,5-hexahydrobenz[cd]indole (4.5 g, 0.016 mol) was halogenated to yield 5.4 g (2aS,4S)-6-bromo compound as an oil.

C.
(2aS,4S)-1-benzoyl-6-bromo-4-(di-n-propylamino)-1,2,2a,3,4,5-hexahydrobenz[cd]indole Using the procedure of Example 7D, the reaction of (2aS,4S)-4-amino-1-benzoyl-6-bromo-1,2,2a,3,4,5-hexahydrobenz[cd]indole (5.4 g, 0.015 mol) with n-propyliodide (10.2 g, 0.06 mol) in the present of $K_2CO_3$ (8.28 g, 0.06 mol) in 200 ml of $CH_3CN$ gave, after chromatography, 3.1 g of product.

D.
(2aS,4S)-1-Benzoyl-6-cyano-4-(di-n-propylamino)-1,2,2a,3,4,5-hexahydrobenz[cd]indole Using the procedure in Example 7E, (2aR,4R)-1-benzoyl-6-bromo-4-(di-n-propylamino)-1,2,2a,3,4,5-hexahydrobenz[cd]indole (3.1 g, 7 mmol) with CuCN (1 g, 21 mmol) and CuI (4 g, 21 mmol) in 100 ml DMF gave 2.5 g of nitrile as an oil.

E.
(2aS,4S)-6-Cyano-4-(di-n-propylamino)-1,2,2a,3,4,5-hexahydrobenz[cd]indole The procedure of Example 7E was followed using 2.5 g (6.5 mmol) of (2aS,4S)-1-benzoyl-6-cyano-4-(di-n-propylamino)-1,2,2a,3,4,5-hexahydrobenz[cd]indole and 8.1 ml (13 mmol) n-butyl lithium to provide 1.6 g of an oil. Chromatography of the oil over silica gel with EtOAc as eluent gave 1 g (54%) of product as an oil.

F.
(2aS,4S)-1-trityl-6-cyano-4-(di-n-propylamino)-1,2,2a,3,4,5-hexahydrobenz[cd]indole The procedure of Example 7G was followed using the product from Example 8E (1. g, 3.5 mmol) to provide 1.6 g of product.

G. Formation of (2aS,4S)-6-acetyl-4-(di-n-propylamino)-1,2,2a,3,4,5-hexahydrobenz[cd]indole The procedure of Example 7H was followed using product from Example 8F (1.6 g, 2.9 mmol) to provide 1.0 g of an oil. Chromatography of the oil over silica gel with EtOAc as eluent gave 700 mg of product. Recrystallization from hexanes yielded 240 mg of the (+) ketone. P mp 85°–86° C.
$[\alpha]_D = +5.15°(CH_3OH)$.

EXAMPLE 9
Preparation of (+)-(2aS,4R)-6-acetyl-4-(di-n-propylamino)-1,2,2a,3,4,5-hexahydrobenz[cd]indole The above described procedure was used to prepare (2aS,4R)-1-benzoyl-6-bromo-4-(di-n-propylamino)-1,2,2a,3,4,5-hexahydrobenz[cd]indole. The procedures of Example 7 were used, except using 1-benzoyl-4,5-(exo)epoxy-1,2,2a,3,4,5-hexahydrobenz[cd]indole instead of the endo epoxy and S-1-phenethylamine instead of the R-1-phenethylamine, to form (+) (2aS,4R)-1-trityl-6-cyano-4-(di-n-propylamine)-1,2,2a,3,4,5-hexahydrobenz[cd]indole (which crystallizes out separately from its enantiomer), a solution of which (2.4 g, 4.6 mmol) in 100 ml of THF was treated with 25 mL of 2.0 M methylmagnesium bromide in diethyl ether. The reaction mixture was refluxed for 16 hr. The reaction mixture was cooled and excess Grignard reagent was decomposed with addition of saturated $NH_4Cl$ solution. The reaction mixture was extracted with ethyl acetate. The organic solution was evaporated to an oil. The oil was dissolved in 25 Ml of 5 N HCl and the solution was stirred at room temperature for 30 min. The acidic solution was made alkaline with the addition of excess concentrated $NH_4OH$ solution. The basic mixture was extracted twice with ethyl acetate. The combined organic solution was washed once with saturated NaCl solution and dried over $MgSO_4$. The ethyl acetate solution was evaporated to yield 1.4 g of an oil. Chromatography of this oil over silica gel with ethyl acetate as eluent gave 1.2 g (87%) of product. Recrystallization from hexane yielded 840 mg of the product (+) ketone.
mp=121°–122° C.
$[\alpha]_D = +66.60°(CH_3OH)$.

EXAMPLE 10
Preparation of (−)-(2aR,4S)-6-acetyl-4-(di-n-propylamino)-1,2,2a,3,4,5-hexahydrobenz[cd]indole The above described procedure was used to prepare (2aR,4S)-1-benzoyl-6-bromo-4-(di-n-propylamino)-1,2,2a,3,4,5-hexahydrobenz[cd]indole. The procedures of Example 7 were used to prepare (2aR,4S)-1-trityl-6- cyano-4-(di-n-propylamino)-1,2,2a,3,4,5-hexahydrobenz[cd]indole a solution of which (3.4 g, 6.5 mmol) in 100 ml of THF was treated with 40 mL of 2.0 M methylmagnesium bromide in diethyl ether. The reaction mixture was refluxed for 16 hr. The reaction mixture was cooled and excess Grignard reagent was decomposed with addition of sat'd NH$_4$Cl solution. The basic mixture was extracted twice with EtOAc. The combined organic solution was washed once with sat'd NaCl solution and dried over MgSO$_4$. The EtOAc solution was evaporated to yield 1.9 g of an oil. Chromatography of this oil over silica gel with EtOAc as eluent gave 1.8 g of product which was recrystallized from hexane to yield 1.4 g of product.

mp 120°-121° C.

$[\alpha]_D = -64.48°(CH_3OH)$.

EXAMPLE 11

Preparation of (+)-(2aS,4R)-6-(2-methylpropanoyl)-4-(di-n-propylamino)-1,2,2a,3,4,5-hexahydrobenz[cd]indole (2aS,4R)-1-trityl-6-cyano-4-(di-n-propylamino)-1,2,2a,3,4,5-hexahydrobenz[cd]indole was prepared as in Example 9. A solution of this hexahydrobenz[cd]indole (9.5 g, 0.018 mmol) in 200 mL of THF was treated with 30 mL of 2.0 M sopropylmagnesium chloride in diethyl ether. The reaction mixture was refluxed for 16 hr. The reaction mixture was cooled and decomposed with addition of 50 mL of 5N HCl then warmed for 30 min on a steam bath. The acidic mixture was extracted twice with EtOAc. The combined organic solution was washed once with sat'd NaCl solution and dried over MgSO$_4$. The EtOAc solution was evaporated to yield 1.9 g of an oil. Chromatography of this oil over silica gel with EtOAc as eluent gave 0.9 g of product. Recrystallization from hexanes yielded 360 mg of product.

mp 87°-89° C.

$[\alpha]_D = +52.72°(CH_3OH)$.

EXAMPLE 12

Preparation of (+)-(2aS,4R)-6-(benzoyl)-4-(di-n-propylamine)1,2-,2a,3,4,5-hexahydrobenz[cd]indole A solution of (+)-(2aS,4R)-1-trityl-6-cyano-4-(di-n-propylamino)-1,2,2a,3,4,5-hexahydrobenz[cd]indole (1.5 g, 2.7 mmol) in 30 mL of THF was treated with 10 mL of 3.0 M phenylmagnesium bromide in diethyl ether. The reaction mixture was refluxed for 16 hr. The reaction mixture was cooled and decomposed with addition of 50 mL of 5N HCl then warmed for 30 min in a steam bath. The acidic mixture was extracted with EtOAc. The acidic solution was made alkaline with the addition of excess conc NH$_4$OH solution. The basic mixture was extracted twice with EtOAc. The combined organic solution was washed once with sat'd NaCl solution and dried over MgSO$_4$. The EtOAc solution was evaporated to yield 0.6 g of an oil. Chromatography of this oil over silica gel with EtOAc as eluent gave 0.3 g of product. Recrystallization from hexanes gave 360 mg (+) ketone.

mp 161°-162° C.

$[\alpha]_D = +93.66°(CH_3OH)$.

EXAMPLE 13

Preparation of (+)-(2aS,4R)-6-(propanoyl)-4-(di-n-propylamino)-1,2,2a,3,4,5-hexahydrobenz[cd]indole A solution of (2aS,4R)-1-trityl-6-cyano-4-di-n-propylamino)-1,2,2a,3,4,5-hexahydrobenz[cd]indole in 200 mL of THF is treated with 25 mL of 2.0 M ethylmagnesium bromide in diethyl ether. The reaction mixture is refluxed for 16 hr. The reaction mixture is cooled and decomposed with addition of 50 mL of 5N HCl then warmed for 30 min on a steam bath. The acidic mixture is extracted twice with EtOAc. The acidic solution is made alkaline with the addition of excess conc NH$_4$OH solution. The basic mixture is extracted twice with EtOAc. The combined organic solution is washed once with sat'd NaCl solution and dried over MgSO$_4$. The EtOAc solution is evaporated to yield an oil. Chromatography of this oil over silica gel with EtOAc as eluent gives product. Recrystallization from hexanes yields (+) ketone.

EXAMPLE 14

Preparation of 2-Di-n-propylamino-8-(isoxazol-5-yl)-1,2,3,4-tetrahydronaphthalene, maleic acid salt A. A solution of n-butyllithium (1.6 M in hexane, 15.1 ml, 24.2 mmol 0 was added to a solution of 8-bromo-2-di-n-propylamine-1,2,3,4-tetrahydronaphthalene (5.0 g, 16.1 mmol) in THF (50 ml) at −78° C. and the reaction stirred at −78° C. for one hour. Gaseous carbon dioxide was bubbled through the reaction at −78° C. until the deep violet color which forms dissipates. Methyllithium (1.4 M in ether, 23 ml) was added. The reaction was stirred a −78° C. for 30 minutes and warmed to room temperature. The reaction was stirred for an additional ten minutes at room temperature at which time the pink color had been lost. An additional 10 ml of the methyllithium solution was added and the reaction became pink once again. After 15 minutes, the pink color was lost an an additional 10 ml of the methylklithium solution added. The reaction was poured onto ice, made acidic with hydrochloric acid ad extracted with ether. The aqueous layer was made basic and extracted with methylenechloride. The basic extracts were dried (Na$_2$SO$_4$) and concentrated to give 3.8 g of crude product. Purification by flash silica gel chromatography using 2:1 hexane"ether containing trace ammonium hydroxide provided 2-di-n-propylamine-8-acetyl-1,2,3,4-tetrahydronaphthalene as a yellow oil (27 g, 61%).

B. A solution of 2-di-n-propylamino-8-acetyl-1,2,3,4-tetrahydronaphthalene (0.3 g, 1.1 mmol), prepared as in Part A hereof, and tris(dimethylamino)-methane (0.32 g, 2.2 mmol) in toluene was heated to reflux for 5 hours and at 60° for 18 hours. An additional aliquot of tris(-dimethylamino)methane (0.16 g, 1.1. mmol) was added and the reaction stirred at 60° for an additional 2 hours. The reaction was concentrated to give 2-di-n-propylamino-8-(1-oxo-3-(dimethylamino)-prop-2-enyl)-1,2,3,4-tetrahydronaphthalene (0.39 g) as a viscous, orange oil.

Hydroxylamine hydrochloride (0.32 g, 4.6 mmol) was added to a solution of 2-di-n-propylamino-8-(1-oxo-3-(dimethylamino)-prop-2-enyl)-1,2,3,4-tetrahydronaphthalene (0.75 g, 2.29 mmol) in acetic acid (5 ml) and the reaction stirred at room temperature. The reaction was concentrated and the residue dissolved in water. This solution was made basic by the addition of concentrated ammonium hydroxide solution and extracted with ether. The extract was washed with brine, dried with Na$_2$SO$_4$, and concentrated to give a viscous, light orange oil. The maleate salt was formed. Crystallization from ethanol/ether gave the title compound as off-white crystals (0.24 g). mp 136°-138°. Recrystallization of this salt from ethanol gave colorless crystals (155 mg). m.p. 139°-141°

Analysis:
Theory: C, 66.65; H, 7.29; N, 6.76;
Found: C, 66.86; H, 7.33; N, 6.79.

EXAMPLE 15

Preparation of
2-Di-n-propylamino-8-isoxazol-3-yl)-1,2,3,4-tetrahydronaphthalene, hydrochloride salt To a solution of 2-di-n-propylamino-8-acetyl-1,2,3,4-tetrahydronaphthalene (3.5 mmol) (prepared as in Part A of Example 14) in methanol (50 ml) was added a solution of hydroxylamine hydrochloride (2.4 g, 35 mmol) in water (10 ml). The solution was stirred at room temperature overnight. The reaction was poured into water, the pH was adjusted to 12 and then extracted with methylene chloride. The extract was dried (Na$_2$SO$_4$) and concentrated to give 1.5 g of a thick oil. Purification by flash chromatography using 3% methanol in methylene chloride containing a trace of ammonium hydroxide and then 5% methanol in methylene chloride containing a trace of ammonium hydroxide as eluting solvent provided 0.98 g of 2-di-n-propylamino-8-(1-oximinoethyl)-1,2,3,4-tetrahydronaphthalene.

2-Di-n-propylamino-8-(1-oximidoethyl)-1,2,3,4-tetrahydronaphthalene (0.8 g; 2.8 mmol) was dissolved in THF, and the solution was cooled to −5° C., after which 9.2 ml (9.7 mmol) of n-butyllithium were added. The mixture became deep red. After stirring for one hour at −5° C., N,N-dimethylformamide was added, and the mixture was stirred at room temperature overnight. The mixture was poured into a solution of 3 g of sulfuric acid in 2 ml of a 4:1 mixture of THF and water. The resulting mixture was refluxed for one hour after which it was Poured into water and the pH was adjusted to 12 with ammonium hydroxide. The mixture was extracted with methylene chloride, and the extract was dried over sodium sulfate and evaporated to give 1.1 g of a residue.

The residue was placed on a silica gel column and was eluted with a 2:1 mixture of hexane and ether containing a trace of ammonium hydroxide. The appropriate fractions were combined to give 210 mg of the free base of the title compound.

The free base was converted to the hydrochloride salt and recrystallized twice from a mixture of methanol and ethyl acetate to give 100 mg of a tan crystalline solid, m.p. 183°-184° C.

Analysis:
Theory: C, 68.14; H, 8.13; N, 8.37;
Found: C, 67.74; H, 8.30; N, 8.20.

EXAMPLE 16

Preparation of
2-Di-n-propylamino-8-pentanoyl-1,2,3,4-tetrahydronaphthalene, oxalate salt n-Butyllithium 93.5 mmole, 3.0 ml, 1.2 M in hexane) was added to a solution of 8-bromo-2-di-n-propylamine-1,2,3,4-tetrahydronaphthalene (1.0 g, 3.2 mmol) in THF (10 ml) at −78° C. The reaction was stirred at −78° C. for 45 minutes and then n-pentanal (0.41 ml, 3.9 mmole) was added. After stirring at −78° C. for 5 minutes, the reaction was warmed to room temperature and poured into dilute HCl solution. The resulting solution was washed once with ether and the ether layer discarded. The aqueous layer was made basic with NH$_4$OH solution and extracted with methylenechloride. The extract was dried (Na$_2$SO$_4$) and concentrated to give 0.95 g of the crude product.

Purification by silica gel flash chromatography using 1:1 ether:hexane with a trace of NH$_4$OH gave 0.68 g of produce MS(FD) m/e=317.

Pyridinium chlorochromate (0.9 g, 4.0 mmol) and 4 Angotrom molecular sieves (30 g) were added to a solution of 2-di-n-propylamine-8-(1'-hydroxy-1-pentyl)-1,2,3,4-tetrahydronaphthalene (0.63 g=2.0 mmol) in methylene chloride (50 ml). The reaction was stirred at room temperature for 1½ hours at which time the reaction was quenched by the addition of methanol (50 ml). Ether was added until the reaction became cloudy and this material was added to the shorted silica gel column and eluted with ether. The eluent was concentrated. Elution of the column was continued with 10% methanol in methylene chloride and the eluent concentrated to give a residue which was triturated with methanol and filtered through Celite. The filtrate was combined with the crude product from the ether elution and concentrated. Purification of this material on a flash silica gel column using 1:3 ether:hexane with a trade of NH$_4$OH provided 240 mg of the title compound. MS(FD): m/e=315. The oxalate salt was formed and crystallized from ethylacetate/hexanes to give 165 mg of white crystals. m.p 107°-108.5° C.

Elemental Analysis:
Theory: C, 68.12; H, 8.70; N, 3,45.
Found: C, 67,85; H, 8,67; N, 3,41.

EXAMPLE 17

Preparation of
2-Di-n-propylamine-8-cyclohexanecarbonyl-1,2,3,4-tetrahydronaphthalene, oxalate salt

Method A

2-Di-n-propylamine-8-bromo-1,2,3,4-tetrahydronaphthalene (1.0 g; 3.2 mmole) was dissolved in 10 ml of THF and cooled to −78° C. after which 2.8 ml of n-butyl-lithium (1.27 M in hexane) were added. The mixture was stirred at −78° C. for 45 minutes after which 0.59 ml (3.5 mmole) of ethyl cyclohexanecarboxylate was added. The mixture was warmed to room temperature and then was poured into a 10% hydrochloric acid solution, washed with ether, the pH adjusted to 10 with ammonium hydroxide, and extracted with methylene chloride. The extract was dried over sodium sulfate and evaporated to give 0.8 g of a residue.

The residue was placed on a silica gel column and was eluted with a 3:1 mixture of hexane and ether containing a trace of ammonium hydroxide. The appropriate fractions were combined to give 0.36 g of the title compound.

Method B

Butyllithium (1.2 M in hexane 3.0 ml, 3.5 mmoles) was added to a solution of 8-bromo-2-di-n-propylamine-1,2,3,4-tetrahydronaphthylene (1.0 g, 3.2 mmole) in THF (10 ml) at −78° C. and stirred for 45 minutes. Cyclohexanecarboxaldehyde (0.47 ml, 3.9 mmole) was added. The reaction was stirred at −78° C. for five minutes, warmed to room temperature, poured into dilute HCl solution and washed with ether. The aqueous layer was made basic with NH₄OH and extracted with methylene chloride. The extract was dried (Na₂SO₄) and concentrated to give 1.1 g of the crude product. The crude product was dissolved in methylene chloride (50 ml) and molecular sieves and pyridinium chlorochromate (1.3 g, 6.4 mmole) added. The reaction was stirred at room temperature for two hours. Methanol (50 ml) was added an the reaction concentrated to provide a slurry. The slurry was dissolved in methylene chloride (50 ml) an enough ether was added to give a cloudy solution. This material was added to a pad of silica gel ad eluted with ether.

The silica gel pad was eluted with 10% methylanol in methylene chloride and the eluent concentrated to give an oil residue. This material was triturated with methanol and filtered through Celite. This filtrate was combined with the ether solution from above and concentrated. This material was dissolved in methylene chloride. Ether was added until the solution became cloudy and then filtered through florisil. The filtrate was concentrated to give 560 mg of an oil which was purified to silica gel flash chromatography using 3:1 hexane:ether containing a trace of NH₄OH as solvent. Appropriate fractions were combined and concentrated to give 350 mg of the desired compound. The oxalate salt was formed and crystallized from ethyl acetate/hexane to give 370 mg of a white solid. m.p. 98.5°-100° C.

Elemental Analysis:
Theory: C, 69.58; H, 8.64; N, 3,25.
Found: C, 69.28; H, 8.87; N, 3.00.

While the invention has been illustrated and described in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. A method for improving primary memory or learning in a mammal, comprising administering to a mammal in need of primary memory or learning improvement a 4-amino benz[cd]indole selected from the group ($\pm$)-4-(di-n-propyl)amino-6-methoxy-1,3,4,5-tetrahydrobenz[cd]indole, ($\pm$)-6-acetyl-4-(di-n-propylamino)-1,3,4,5-tetrahydrobenz[cd]indole, ($\pm$)-6-(2,2-dimethylpropanoyl)-4-(di-n-propylamino)-1,3,4,5-tetrahydrobenz[cd]indole, (2aS,4R)-,(2aR,4S)-6-acetyl-4-(di-n-propylamino)-1,2,2a,3,4,5-hexahydrobenz[cd]-indole, (2aR,4R)-6-acetyl-4-(di-n-propylamino)-1,2,2a,3,4,5-hexahydrobenz[cd]indole, (2aS,4S)-6-acetyl-4-(di-n-propylamino)-1,2,2a3,4,5-hexahydrobenz[cd]indole, (+)-(2aS,4R)-6-acetyl-4-(di-n-propylamino)-1,2,2a,3,4,5-hexahydrobenz[cd]indole, (−)-2aR,4S)-6-acetyl-4-(di-n-propylamino)-1,2,2a,3,4,5-hexahydrobenz[cd]indole, (+)-(2aS,4R)-6-(2-methylpropanoyl)-4-(di-n-propylamino)-1,2,2a,3,4,5-hexahydrobenz[cd]indole, (+)-(2aS,4R)-6-(benzoyl)-4-(di-n-propylamine)-1,2,2a,3,4,5-hexahydrobenz[cd]indole, and (+)-(2aS,4R)-6-(propanoyl)-4-(di-n-propylamino)-1,2,2a,3,4,5-hexahydrobenz[cd]indole, or a pharmaceutically acceptable salt thereof, which is a 5-hydroxytryptamine receptor agonist selective for the 5-hydroxytryptamine-1A subtype, at a dose effective for improving primary memory or learning.

2. The method of claim 1, wherein the mammal is in need of memory improvement and said dose is effective for improving primary memory.

3. The method of claim 1, wherein the mammal is in need of learning improvement and said dose is effective for improving learning.

4. The method of claim 1, wherein the mammal is in need of primary memory improvement and said dose is effective for improving primary memory.

5. The method of claim 1, wherein the mammal is in need of learning improvement and said dose is effective for improving learning.

6. The method of claim 4, wherein the 5-hydroxytryptamine-1A receptor agonist is ($\pm$)-4-(di-n-propyl)amino-6-methoxy-1,3,4,5-tetrahydrobenz[cd]indole.

7. The method of claim 5, wherein the 5-hydroxytryptamine-1A receptor agonist is ($\pm$)-4-(di-n-propyl)amino-6-methoxy-1,3,4,5-tetrahydrobenz[cd]indole.

8. A method of inducing hippocampal theta rhythm in a mammal, comprising administering to a mammal in need of hippocampal theta rhythm induction an effective amount of a 4-amino benz[cd]indole selected from the group ($\pm$)-4-(di-n-propyl)amino-6-methoxy-1,3,4,5-tetrahydrobenz[cd]indole, ($\pm$)-6-acetyl-4-(di-n-propylamino)-1,3,4,5-tetrahydrobenz[cd]indole, ($\pm$)-6-(2,2-dimethylpropanoyl)-4-(di-n-propylamino)-1,3,4,5-tetrahydrobenz[cd]indole, (2aS,4R)-,(2aR,4S)-6-acetyl-4-(di-n-propylamino)-1,2,2a,3,4,5-hexahydrobenz[cd]indole, (2aR,4R)-6-acetyl-4-(di-n-propylamino)-1,2,2a,3,4,5-hexahydrobenz[cd]indole, (2aS,4S)-6-acetyl-4-(di-n-propylamino)-1,2,2a,3,4,5-hexahydrobenz[cd]indole, (+)-(2aS,4R)-6-acetyl-4-(di-n-propylamino)-1,2,2a,3,4,5-hexahydrobenz[cd]indole, (−)-(2aR,4S)-6-acetyl-4-(di-n-propylamino)-1,2,2a,3,4,5-hexahydrobenz[cd]indole, (+)-(2aS,4R)-6-(2-methylpropanoyl)-4-(di-n-propylamino)-1,2,2a,3,4,5-hexahydrobenz[cd]indole, (+)-(2aS,4R)-6-(benzoyl)-4-(di-n-propylamine)-1,2,2a,3,4,5-hexahydrobenz[cd]indole, and (+)-(2aS,4R)-6-(propanoyl)-4-(di-n-propylamino)-1,2,2a,3,4,5-hexahydrobenz[cd]indole, or a pharmaceutically acceptable salt thereof, which is a 5-hydroxytryptamine receptor agonist selective for the 5-hydroxytryptamine-1A subtype.

9. The method of claim 8, wherein the 5-hydroxytryptamine-1A receptor agonist is ($\pm$)-4-(di-n-propyl)amino-6-methoxy-1,3,4,5-tetrahydrobenz[cd]indole.

* * * * *

UNITED STATES PATENT AND TRADEMARK OFFICE
CERTIFICATE OF CORRECTION

PATENT NO. : 5,292,766
DATED : March 8, 1994
INVENTOR(S) : James A. Clemens

It is certified that error appears in the above-identified patent and that said Letters Patent is hereby corrected as shown below:

In column 1, line 27, please delete "special" and insert --Special--.

In column 1, line 32, please delete "ElectroencePha-" and insert --Electroencepha--.

In column 4, line 2, please delete "Pharmaceutical" and insert --pharmaceutical--.

In column 9, line 44, please delete "38-H" and insert in --3ß-H--.

In column 11, line 4, please delete "equal." and insert "equal".

In column 14, line 21, please delete the "P" prior to "mp".

In column 15, line 28, please delete "sopropylmagnesium" and --isopropylmagnesium--.

In column 17, line 42, please delete "Poured" and insert in --poured--.

Signed and Sealed this

Twenty-eighth Day of June, 1994

Attest:

BRUCE LEHMAN

Attesting Officer   Commissioner of Patents and Trademarks